(12) United States Patent
Keren et al.

(10) Patent No.: US 10,463,397 B2
(45) Date of Patent: Nov. 5, 2019

(54) SYSTEMS, DEVICES, AND METHODS FOR HAIR IMPLANTATION

(71) Applicant: Hairstetics, Ltd., Herzliya (Pituach) (IL)

(72) Inventors: Dvir Keren, Tel Aviv (IL); Boaz Shenhav, Tel Aviv (IL)

(73) Assignee: HAIRSTETICS, LTD., Herzliya (Pituach) (IL)

( * ) Notice: Subject to any disclaimer, the term of this patent is extended or adjusted under 35 U.S.C. 154(b) by 57 days.

(21) Appl. No.: 15/329,967

(22) PCT Filed: Jul. 28, 2015

(86) PCT No.: PCT/IB2015/001780
§ 371 (c)(1),
(2) Date: Jan. 27, 2017

(87) PCT Pub. No.: WO2016/016722
PCT Pub. Date: Feb. 4, 2016

(65) Prior Publication Data
US 2017/0265896 A1   Sep. 21, 2017

Related U.S. Application Data

(60) Provisional application No. 62/029,827, filed on Jul. 28, 2014.

(51) Int. Cl.
*A61F 2/10* (2006.01)
*A61B 17/34* (2006.01)
(Continued)

(52) U.S. Cl.
CPC ............ *A61B 17/3468* (2013.01); *A61F 2/10* (2013.01); *A61B 17/205* (2013.01);
(Continued)

(58) Field of Classification Search
CPC ..... A61B 2017/0403; A61B 2017/0445; A61F 2240/00; A61F 2240/001; A61F 2/10
See application file for complete search history.

(56) References Cited

U.S. PATENT DOCUMENTS 4,216,777 A    8/1980  Pridemore
5,417,683 A    5/1995  Shiao
(Continued)

FOREIGN PATENT DOCUMENTS

WO    WO 2014/136119 A1    9/2014

OTHER PUBLICATIONS

International Search Report and Written Opinion dated May 6, 2016 in corresponding PCT International Application.

*Primary Examiner* — Christopher D. Prone
(74) *Attorney, Agent, or Firm* — Finnegan, Henderson, Farabow, Garrett & Dunner, L.L.P.

(57) ABSTRACT

A hair anchor prepared by a process whereby a plurality of hair anchors are formed from a single elongated metal tube according to some embodiments of the present disclosure may include forming at least two slits in an elongated direction of the elongated metal tube, each slit spanning prospective end portions of at least two hair anchors; and severing the elongated metal tube at an intermediate location along the at least two slits such that a first portion of each of the at least two slits is contained in one of the at least two hair anchors and a second portion of each of the at least two slits remains attached to the elongated metal tube for inclusion in a subsequent hair anchor to be later severed from the elongated metal tube.

12 Claims, 8 Drawing Sheets

FIG. 13

(51) Int. Cl.
 *A61B 17/00* (2006.01)
 *A61B 17/20* (2006.01)

(52) U.S. Cl.
 CPC ............... *A61B 2017/00526* (2013.01); *A61B 2017/00752* (2013.01); *A61F 2240/001* (2013.01)

(56) References Cited

U.S. PATENT DOCUMENTS

| | | | | |
|---|---|---|---|---|
| 5,611,810 A | * | 3/1997 | Arnold | A61B 17/3468 606/167 |
| 6,461,369 B1 | | 10/2002 | Kim | |
| 2002/0082627 A1 | * | 6/2002 | Berg | A61B 17/0057 606/155 |
| 2003/0093087 A1 | * | 5/2003 | Jones | A61B 17/22031 606/108 |
| 2003/0212418 A1 | * | 11/2003 | Yencho | A61B 17/0644 606/153 |
| 2005/0267524 A1 | * | 12/2005 | Chanduszko | A61B 17/0057 606/213 |
| 2007/0067034 A1 | * | 3/2007 | Chirico | A61B 17/70 623/17.11 |
| 2007/0073337 A1 | * | 3/2007 | Abbott | A61B 17/0057 606/213 |
| 2007/0179530 A1 | * | 8/2007 | Tieu | A61B 17/0487 606/232 |
| 2007/0288038 A1 | * | 12/2007 | Bimbo | A61B 17/221 606/127 |
| 2008/0132894 A1 | * | 6/2008 | Coilard-Lavirotte | A61B 17/1604 606/60 |
| 2008/0208265 A1 | * | 8/2008 | Frazier | A61B 17/0401 606/326 |
| 2009/0088677 A1 | * | 4/2009 | Cohen | A61F 11/002 604/8 |
| 2010/0163054 A1 | * | 7/2010 | Breznel | A61B 17/12022 128/831 |
| 2010/0312259 A1 | * | 12/2010 | Houser | A61B 17/0057 606/142 |
| 2011/0011917 A1 | * | 1/2011 | Loulmet | A61B 17/0401 227/181.1 |
| 2012/0245612 A1 | | 9/2012 | Keren et al. | |
| 2013/0226214 A1 | | 8/2013 | Okuda | |
| 2014/0188150 A1 | | 7/2014 | Oc et al. | |
| 2015/0073478 A1 | * | 3/2015 | Belson | A61B 17/0401 606/232 |
| 2015/0250493 A1 | * | 9/2015 | Umar | A61B 17/32053 606/133 |

* cited by examiner

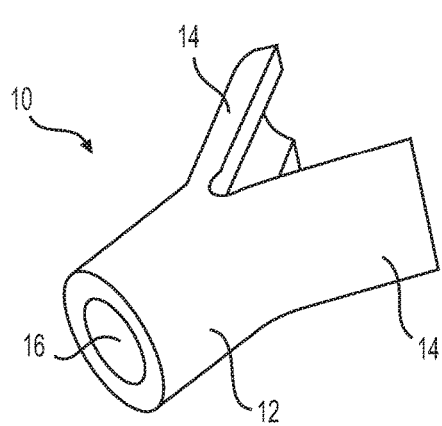
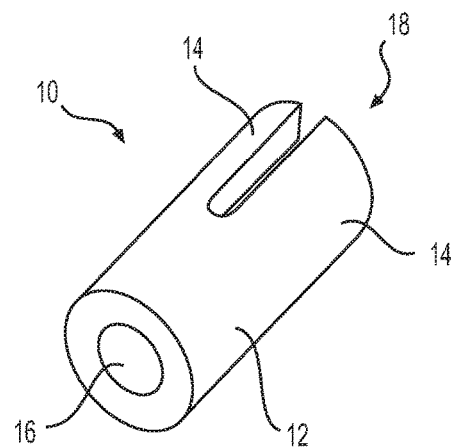
FIG. 1
FIG. 2
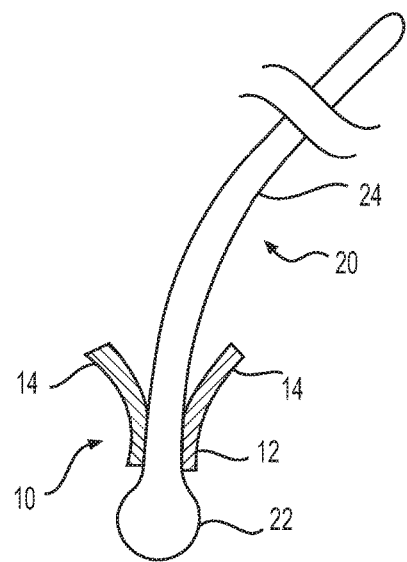
FIG. 3

SYSTEMS, DEVICES, AND METHODS FOR HAIR IMPLANTATION

RELATED APPLICATIONS

This application is a National Stage Entry of International Application No. PCT/IB2015/001780, filed Jul. 28, 2015, which claims priority to U.S. Provisional Application No. 62/029,827, filed Jul. 28, 2014, which is incorporated herein by reference in its entirety.

TECHNICAL FIELD

Embodiments of the present disclosure generally relate to systems, devices, and methods for hair implantation. More particularly, embodiments of the present disclosure relate to systems and devices used in hair implantation procedures, and methods of forming these systems and devices.

BACKGROUND

Baldness remains a common problem for many men and women all around the world. As a result, many patients experiencing baldness often seek ways to treat hair loss. There are several known treatments for hair loss, including both surgical and non-surgical treatments.

One non-surgical treatment is for the patient to use any one of the many commercial products that have chemical solutions used to regrow hair over time. This treatment is limited, however, because it does not work for all patients, nor does it provide a permanent solution to hair loss. Another non-surgical treatment is for the patient to wear a wig or toupee. This treatment is also limited because it generally provides poor aesthetic results and also does not provide a permanent solution to hair loss.

One surgical treatment is for the patient to undergo a hair implant procedure. The hair implant procedure can include surgically moving a patient's own hair from one location to another. While this treatment can provide a permanent solution to hair loss, it may be less than adequate from medical and aesthetic perspectives. Some prior attempts at synthetic hair implants employed configurations that have led to infection or other sub-optimal results.

SUMMARY

A hair implantation assembly according to some embodiments of the present disclosure may include a plurality of hair strands and a plurality of hair anchors, each hair anchor retaining a single hair strand and having at least one resilient member associated therewith; a plurality of lumens, each lumen containing a single hair anchor in a manner that compresses an associated at least one resilient member toward an insertion axis of each lumen; and a plurality of pushers, each pusher associated with one of the plurality of lumens, and configured to simultaneously expel the plurality of hair anchors into target tissue, wherein the plurality of lumens and the plurality of pushers are configured to cooperate to cause the plurality of resilient members to simultaneously move away from the insertion axis of each lumen when expelled into the target tissue.

In some embodiments, the hair implantation assembly may further include one or more of the following features. The plurality of hair strands may include at least 25 hair strands, the plurality of lumens may include at least 25 lumens, the plurality of hair anchors may include at least 25 self-expanding hair anchors, and the plurality of pushers may include at least 25 pushers. The plurality of lumens may be configured to cause the plurality of hair strands to be implanted into the target tissue at a substantially common angle. The substantially common angle may be a non-90 degree angle. The hair implantation assembly may further include a deployment mechanism for transferring a deployment force simultaneously to each of the plurality of pushers. The hair implantation assembly may further include a plunger configured to simultaneously convey an anchor expulsion force to each hair anchor within the plurality of lumens. The hair implantation assembly may further include an opening in a side of the plunger through which the plurality of hair strands pass. The hair implantation assembly may further include a hair holder configured to hold the plurality of hair strands passing through the opening. The hair holder may include a slit configured apply friction on the hair strands to resist sliding of the plurality of hair strands. The plurality of lumens may be associated with a plurality of needles, and wherein each needle has a tip that is cut at an angle enabling skin penetration when an axial force is applied thereto. The plurality of needles may be arranged in a single-file row. The plurality of pushers may be configured to expel the plurality of hair anchors in a row, substantially along a line. The line may be substantially straight. The needles may be arranged such that a piercing edge on each needle is located at a substantially common rotational orientation with respect to a piercing edge of each other needle. The plurality of needles may be oriented at a substantially common non-90 degree angle to cause the plurality of hair strands to extend from a surface of the target tissue at the substantially common non-90 degree angle. The hair implantation assembly may further include a housing having a bottom through which the plurality of needles are configured to extend, and wherein the common non-90 degree angle is with respect to a bottom of the housing. The hair implantation assembly may further include a contact surface configured to engage with skin covering the target tissue, wherein the plurality of needles are oriented at the common non-90 degree angle with respect to the contact surface. The hair strands may be constructed of a synthetic material. Each of the plurality of hair strands may be threaded through a corresponding hair anchor, lumen, and pusher.

Additional embodiments consistent with the present disclosure may include a hair implantation assembly for inserting hair strands into target tissue at anon-90 degree angle with respect to a surface of the target tissue. The hair implantation assembly may include a contact surface configured to engage with skin covering the target tissue; a plurality of hollow needles oriented at a substantially common non-90 degree angle with respect to the contact surface; a plurality of hollow needle tips cut at angles enabling skin penetration when axial forces are applied to each of the plurality of hollow needles; a plurality of hair anchors, each hair anchor contained within one of the plurality of hollow needles; a plurality of hair strands, each hair strand being contained within one of the plurality of hair anchors; and a plurality of pushers, each pusher associated with one of the plurality of hollow needles for expelling the plurality of hair anchors along the substantially common non-90 degree angle to cause the plurality of hair strands to extend from the skin at the substantially common non-90 degree angle.

Additional embodiments consistent with the present disclosure may include a hair implantation assembly. The hair implantation assembly may include a plurality of hair strands; a plurality of hollow needles, each hollow needle containing an anchor holding a single one of the plurality of hair strands; a plunger configured to simultaneously convey an anchor expulsion force to each anchor within the plurality of hollow needles; and an opening in a side of the plunger through which the plurality of hair strands pass.

Additional embodiments consistent with the present disclosure may include a hair implantation assembly. The hair implantation assembly may include a plurality of hollow needles spaced from each other substantially in at least one line, each of the plurality of needles including a hollow needle tip cut at an angle enabling skin penetration when an axial force is applied thereto; a plurality of hair anchors, each hair anchor contained within one of the plurality of hollow needles; a plurality of hair strands, each hair strand being contained within one of the plurality of hair anchors; and a plurality of pushers, each pusher associated with one of the plurality of hollow needles for expelling the plurality of hair anchors in at least one row, substantially along the at least one line. The at least one line may be only one line and the at least one row may be only one row.

Additional embodiments consistent with the present disclosure may include a hair implantation assembly. The hair implantation assembly may include a plurality of hollow needles arranged in an array; a plurality of hollow needle tips on the plurality of needles, the tips being cut so as to form a piercing edge on each needle at location at a circumferential position on each hollow needle; a support having openings through with the needles are configured to pass, wherein the needles are arranged to pass through the support such that the piercing edge on each needle is located at a substantially common rotational orientation with respect to the piercing edge of each other hollow needle; a plurality of hair anchors, each hair anchor contained within one of the plurality of hollow needles; a plurality of hair strands, each hair strand being contained within one of the plurality of hair anchors; and a plurality of pushers, each pusher associated with one of the plurality of hollow needles for expelling the plurality of hair anchors from the hollow needles.

Additional embodiments consistent with the present disclosure may include a hair anchor prepared by a process whereby a plurality of hair anchors are formed from a single elongated metal tube. The process may include forming at least two slits in an elongated direction of the elongated metal tube, each slit spanning prospective end portions of at least two hair anchors; and severing the elongated metal tube at an intermediate location along the at least two slits such that a first portion of each of the at least two slits is contained in one of the at least two hair anchors and a second portion of each of the at least two slits remains attached to the elongated metal tube for inclusion in a subsequent haft anchor to be later severed from the elongated metal tube.

In some embodiments, the hair anchor may further include one or more of the following features. Forming the at least two slits may include laser cutting the at least two slits into the elongated metal tube. The process may further include inserting a hair strand into the elongated metal tube prior to severing the elongated metal tube. The at least two slits may cooperate to define at least two resilient members. The hair anchor may further include a tubular body portion undissected by the at least two slits, and wherein the at least two resilient members may be integral with and extend from the tubular body portion. The process may further include forming a slot at the intermediate location along each slit, the slot being configured to facilitate severing of the metal tube at the intermediate location. The process may further include forming at least one burr upon severance at the intermediate location. The process may further include forming a notch in the elongated metal tube between two adjacent tubular body portions, and wherein the notch may be configured to facilitate severing of the elongated metal tube at a location of the notch. The process may further include forming a burr at a location of severance of the notch. The at least two resilient members may extend between two tubular body portions of two prospective hair anchors prior to severing at the intermediate location. The process may further include deforming the at least two resilient members to cause the at least two resilient members to diverge from a longitudinal axis of the elongated metal tube prior to severing the elongated metal tube at the intermediate location. Forming at least two slits may include cutting a first slit in a wall of the elongated metal tube, the first slit extending generally in a direction of a longitudinal axis of the elongated metal tube, and cutting a second slit in the tube wall, the second slit generally opposing the first slit.

Additional embodiments consistent with the present disclosure may include a process of forming a plurality of hair anchors from a single elongated metal tube. The process may include forming at least two slits in an elongated direction of the elongated metal tube, each slit spanning prospective end portions of at least two hair anchors; and severing the elongated metal tube at an intermediate location along the at least two slits such that a first portion of each of the at least two slits is contained in one of the at least two hair anchors and a second portion of each of the at least two slits remains attached to the elongated metal tube for inclusion in a subsequent hair anchor to be later severed from the elongated metal tube.

In some embodiments, the process may further include one or more of the following features. The process may further include laser cutting the at least two slits into the elongated metal tube. The process may further include inserting a hair strand into the elongated metal tube prior to severing the elongated metal tube. The at least two slits may cooperate to define at least two resilient members the hair anchor. A tubular body portion may be undissected by the at least two slits, and wherein the at least two resilient members may be integral with and extend from the tubular body portion. The process may further include forming a slot across the intermediate location along each slit, the slot being configured to facilitate severing of the metal tube at the intermediate location. The process may further include forming at least one burr upon severance at the intermediate location. The process may further include forming a notch between two adjacent tubular body portions in the elongated metal tube, and wherein the notch is configured to facilitate severing of the elongated metal tube at a location of the notch. The process may further include forming at least one burr at a location of severance of the notch. Prior to severing at the intermediate location, the at least two resilient members may extend between two tubular body portions of two prospective hair anchors. The process may further include deforming the at least two resilient members to cause the at least two resilient members to diverge from a longitudinal axis of the elongated metal tube prior to severing the elongated metal tube at the intermediate location. The process may further include cutting a first slit in a wall of the elongated metal tube, the first slit extending generally in a direction of a longitudinal axis of the elongated metal tube, and cutting a second slit in the tube, the second slit generally opposing the first slit.

Additional embodiments consistent with the present disclosure may include a hair anchor having a tubular body, a first resilient member extending from the body, a second resilient member extending from the body, a first burr on a distal end of the first resilient member, and a second burr on a distal end of the second resilient member.

In some embodiments, the hair anchor may further include one or more of the following features. The first and second burrs may be formed by severing the hair anchor from an elongated metal tube. The hair anchor May further include at least one hair strand threaded through the tubular body prior to severing the hair anchor from the elongated metal tube. A nodule may be formed on an end of the at least one hair strand for preventing the end from passing through the tubular body. The first and second resilient members may be integrally formed with the body. The hair anchor may further include a third burr on the body. The third burr may be located on a side of the hair anchor opposite the first and second burrs. The body may have an outer diameter of about 0.15-0.25 mm. An opening associated with the body may have a diameter of about 0.07-0.18 mm. A shaft of the at least one hair strand may have a diameter of 0.05-0.15 mm, and an implant end of the at least one hair strand may have a diameter of 0.15-0.26 mm.

Additional embodiments consistent with the present disclosure may include a process of forming a hair anchor from a single elongated metal tube. The process may include forming at least two slits in the elongated metal tube, the at least two slits defining at least two resilient members extending from a body of the hair anchor, wherein the body is unperforated by the two slits; and severing the elongated metal tube at an intermediate location along the at least two slits, wherein severing is performed in a manner resulting in formation of at least one burr on a distal end of at least one resilient member.

In some embodiments, the process may further include one or more of the following features. Forming the at least one burr may include forming first and second burrs on the at least two resilient members during severing. The process may further include threading at least one hair strand through the body prior to severing the hair anchor from the elongated metal tube. The process may further include forming a nodule on an end of the at least one hair strand. The process may further include forming a third burr on the body by severing the body from the metal tube. The third burr may be located on a side of the hair anchor opposite the first and second burrs. The at least two resilient members may be integrally formed with the body. The body may have an outer diameter of about 0.15-0.25 mm. An opening associated with the body may have a diameter of about 0.07-0.18 mm. A shaft of the at least one hair strand may have a diameter of 0.05-0.15 mm, and an implant end of the at least one hair strand may have a diameter of 0.15-0.26 mm.

Additional embodiments consistent with the present disclosure may include a hair implant device prepared by a process. The process may include obtaining a strand of material for use in a hair implant procedure; subjecting an end of the strand to a treatment that causes a physical deformation of the strand in order to cause a nodule on the end of the strand, the nodule having a width greater than a width of the strand; and threading the strand through a hair anchor having a channel extending therethrough and having a channel opening, the channel opening having a width smaller than the width of the nodule to thereby inhibit the end of the strand from being pulled through the opening.

In some embodiments, the hair implant device may further include one or more of the following features. The strand may include a natural hair. The strand may include a synthetic hair. Subjecting the end of the strand to the treatment may include heating the end of the strand. Heating the end of the strand may include heating the end of the strand to a temperature above a melting temperature of the strand. Heating the end of the strand may include heating the end of the strand to temperature above a glass transition temperature of the material but below a melting temperature of the material. The process may further include applying force to the heated region. Subjecting the end of the strand to the treatment may include melting the end of the strand. The process may further include coating the end of the strand with Paraylene. The process may further include bonding the end of the strand with a portion of another strand. The nodule may be a bulbous shape.

Additional embodiments consistent with the present disclosure may include a process of forming a hair implant device. The process may include obtaining a strand of material for use in a hair implant procedure; subjecting an end of the strand to a treatment that causes a physical deformation of the strand in order to cause a nodule on the end of the strand, the nodule having a width greater than a width of the strand; and threading the strand through a hair anchor having a channel extending therethrough and having a channel opening, the channel opening having a width smaller than the width of the nodule to thereby inhibit the end of the strand from being pulled through the opening.

In some embodiments, the process may further include one or more of the following features. The strand may include a natural hair. The strand may include a synthetic hair. Subjecting the end of the strand to the treatment may include heating the end of the strand. Heating the end of the strand may include heating the end of the strand to a temperature above a melting temperature of the strand. Heating the end of the strand may include heating the end of the strand to temperature above a glass transition temperature of the material but below a melting temperature of the material. The process may further include applying force to the heated region. Subjecting the end of the strand to the treatment may include melting the end of the strand. The process may further include coating the end of the strand with Paraylene. The process may further include bonding the end of the strand with a portion of another strand. The nodule may be a bulbous shape.

Additional embodiments consistent with the present disclosure may include a synthetic hair including a shaft made of a synthetic material, the shaft having a first crystalline structure; and a nodule integrally formed on a distal end region of the shaft and being formed of the synthetic material, wherein the nodule has a second crystalline structure differing from the first crystalline structure.

In some embodiments, the synthetic hair may further include one or more of the following features. The nodule may be formed by heating the shaft. The nodule may be a bulbous shape. An anchor may have an opening therethrough and wherein the shaft may extend through the opening and the nodule may have a size greater than a size of the opening to thereby cause the anchor to retain the synthetic hair. A crystalline structure level in the shaft may be higher than a crystalline structure level in the nodule. A crystalline structure level in the shaft may be at least 30% higher than a crystalline structure level in the nodule. A crystalline structure level in the shaft may be approximately 50% higher than a crystalline structure level in the nodule. The shaft may have molecules aligned generally in a longitudinal direction of the shaft. The nodule may have molecules that are generally unaligned with the longitudinal direction of the shaft. The shaft may have a higher percent of aligned molecules than a percentage of aligned molecules in the nodule. A tensile strength of the shaft may be greater than a tensile strength of the nodule. The shaft may have a greater transparency than a transparency of the nodule. A molecular weight of molecules in the nodule may be lower than a molecular weight of molecules in the shaft. A tear force of the shaft may be greater than 300 grams. A tear force of the shaft may be between 300 and 700 grams. A tear force of the shaft may be greater than 500 grams.

Additional embodiments consistent with the present disclosure may include a hair implant device for aesthetic hair augmentation. The hair implant device may include at least one hair strand having an implant end configured for implantation in target tissue and a shaft configured to extend through the target tissue to a location external to a subject individual; at least one anchor body connected to the implant end of the at least one hair strand; and at least one resilient metal member connected to the at least one anchor body and configured to flex in a direction away from an axis of the at least one anchor body upon implantation into the target tissue to thereby resist removal of the hair strand from the target tissue when forces are exerted on the hair strand from a location external to the subject individual.

In some embodiments, the hair implant device may further include one or more of the following features. The target tissue may be scalp tissue. The target tissue may be eyebrow tissue. The at least one hair strand may include a natural hair. The at least one strand may include a synthetic hair. The anchor body may include a tube, and wherein the at least one hair strand may extend through at least a portion of the tube. The may include a plurality of slits therein. The hair implant device may further include a plurality of needles and wherein the at least one anchor body includes a plurality of anchor bodies each retained within an individual one of the plurality of needles, and a plurality of simultaneously actuatable pushers configured to simultaneously expel into the target tissue the plurality of anchor bodies from the plurality of needles. The boundaries of the at least one resilient metal member may be defined by the slits. The at least one resilient metal member may be integrally formed with the at least one anchor body. The at least one anchor body and the at least one resilient metal member may be formed of a shape memory alloy. The shape memory alloy may include nitinol. The at least one resilient metal member may include two resilient metal members each formed by slits in the tube. The slits may be laser cut. The at least one anchor body may include an opening therein, and wherein the at least one hair strand may include on an end thereof a region wider than the opening. The at least one anchor body may include a tube having an elongated channel therethrough, the channel may have a width of less than about 120 µm. The at least one anchor body may be configured for delivery through a needle in a manner such that walls of the needle maintain the at least one resilient member in a non-expanded position prior to implantation, and wherein the at least one resilient member is configured to flex away from the at least one anchor body upon expulsion from the needle. The at least one hair strand may have a strand diameter and include a deformation on an end thereof, such that the deformation may have a deformation width greater than the strand diameter. The deformation may be formed by heating. The opening may extend all the way through the channel of the at least one anchor body. The at least one anchor body and the at least one resilient member may be coated with Paraylene. The anchor may be configured for delivery through a hollow needle. The resilient member may be configured to flex outwardly in response to a force exerted thereon by a deployment mechanism. The at least one hair strand may include at least 36 hair strands, and wherein the at least one anchor body may include at least 36 anchor bodies. The at least one anchor body may include a tube having a channel therein for retaining the implant end of the hair strand, wherein the at least one anchor body may have a rigidity substantially greater than a rigidity of the at least one hair strand, and wherein the at least one resilient member may have a rigidity substantially greater than the rigidity of the hair strand, and may be configured to selectively flex in a direction away from an axis of the anchor body upon implantation into the target tissue. An end portion of the shaft may have end width greater than the shaft width. The hair implant device may further include a hair implant anchor having a hair holder portion for retaining the end portion of the hair strand, the hair holder portion having an opening therein smaller than the shaft width to thereby inhibit the end portion from being pulled through the opening. The hair holder portion and the at least one deployable leaf may be configured to be contained within a lumen to be inserted into the target tissue and to be expelled from the lumen in the target tissue, the deployable leaf may be configured to be compressed toward the insertion axis when within the lumen and to expand in a direction away from the insertion axis upon expulsion from the lumen, to thereby secure the hair implantation assembly to the target tissue while the strand extends through the target tissue to a location external to the subject individual.

Additional embodiments consistent with the present disclosure may include a hair implant device for aesthetic hair augmentation. The hair implant device may include at least one hair strand having an implant end configured for implantation in target tissue and a shaft configured to extend through the target tissue to a location external to a subject individual; at least one anchor body configured for implantation in the target tissue, the at least one anchor body including a tube having a channel therein for retaining the implant end of the hair strand; and at least one resilient member configured to flex in a direction away from the at least one anchor body upon implantation into the target tissue, wherein the device is configured such that upon implantation, the at least one hair strand extends through at least a portion of the channel of the tube, through the target tissue, and to a location external to the subject individual.

In some embodiments, the hair implant device may further include one or more of the following features. The channel of the tube may have a width that is no greater than about 1½ times the width of a human hair. The tube may be substantially cylindrical and may be configured to be contained within a hollow needle prior to implantation. The at least one resilient member may be configured to be retained within the needle and to self-expand upon expulsion from the needle. The at least one resilient member may include at least two spring-biased leafs. The at least two spring biased leafs may be integrally formed with the tube. The at least two spring biased leafs may be cut into the tube. The anchor body and the at least one resilient member may be made of metal. The anchor body and the at least one resilient member may be coated with Paraylene. The channel may extend through the tube and wherein the at least one hair strand may have a width on an end thereof greater than a width of the channel. The hair implant device may further include a plurality of needles and wherein the at least one anchor body may include a plurality of anchor bodies each retained within an individual one of the plurality of needles, and a plurality of simultaneously actuatable pushers configured to simultaneously expel into the target tissue the plurality of anchor bodies from the plurality of needles.

Additional embodiments consistent with the present disclosure may include a hair implant device for aesthetic hair augmentation. The hair implant device may include at least one hair strand having an implant end configured far implantation in target tissue and a shaft configured to extend through the target tissue to a location external to a subject individual; at least one anchor body for retaining the at least one hair strand, the at least one anchor body having a rigidity substantially greater than a rigidity of the at least one hair strand and being configured for implantation in the target tissue; and at least one resilient member connected to the at least one anchor body, the at least one resilient member having a rigidity substantially greater than the rigidity of the hair strand, and being configured to selectively flex in a direction away from an axis of the anchor body upon implantation into the target tissue, wherein the device is configured such that upon anchor body implantation, the at least one hair strand extends through at least a portion of the channel of the tube, through the target tissue, and to a location external to the subject individual.

In some embodiments, the hair implant device may further include one or more of the following features. The at least one hair stand may be composed of a first material, and the anchor body and the at least one resilient member may be composed of a second material, different from the first material. The hair strand may be approximately a thickness of a human hair and may be contained in an opening in the anchor body, the opening having a thickness of no greater than about one and a half times the thickness of a human hair. The anchor may be made of metal. The metal may include a shape memory alloy. The metal may include nitinol. The at least one hair strand and the anchor may be coated with Paraylene. The at least one resilient member may include at least two spring biased leafs. The anchor body may include a tube. The tube may have a channel therethough. The at least one hair strand may extend through the channel.

Additional embodiments consistent with the present disclosure may include a hair implant device for aesthetic hair augmentation and for insertion into target tissue of a subject individual along an insertion axis. The hair implant device may include at least one hair strand configured for implantation in target tissue, the hair strand having a shaft configured to extend through the target tissue to a location external to a subject individual, the shaft having a shaft width; an end portion on the at least one hair strand, the end portion having an end width greater than the shaft width; a hair implant anchor having a hair holder portion for retaining the end portion of the hair strand, the hair holder portion having an opening therein smaller than the shaft width to thereby inhibit the end portion from being pulled through the opening; and at least one deployable leaf connected to the hair holder portion, wherein the hair holder portion and the at least one deployable leaf are configured to be contained within a lumen to be inserted into the target tissue and to be expelled from the lumen in the target tissue, the deployable leaf being configured to be compressed toward the insertion axis when within the lumen and to expand in a direction away from the insertion axis upon expulsion from the lumen, to thereby secure the hair implantation assembly to the target tissue while the strand extends through the target tissue to a location external to the subject individual.

In some embodiments, the hair implant device may further include one or more of the following features. The hair holder portion and the at least one deployable leaf may be integrally formed. The hair holder portion and the at least one deployable leaf may be made of a material having a rigidity substantially greater than a rigidity of the hair strand. The hair holder portion and the at least one deployable leaf may be made of metal. The metal may be nitinol. The hair implant anchor may include a tube. The at least one deployable leaf may be formed by cutting slits in the tube and thereafter deforming the tube. The end portion may be in a shape of a bulb. The end portion may be formed by heating an end of the at least one hair shaft.

Methods consistent with embodiments of the present disclosure may include positioning a plurality of needles over a hair implantation site, each needle containing a hair anchor and at least one hair strand associated with the hair anchor; penetrating skin of the implantation site with the plurality of needles along a penetration axis associated with each needle such that each needle reaches an implantation depth; and expelling from each of the plurality of needles at the implantation depth, a hair anchor and an associated hair strand such that upon expulsion at least one resilient member of each hair anchor moves away from the penetration axis to secure each hair anchor to the target tissue.

In some embodiments, the method may include one or more of the following features. The hair strand may be natural or synthetic. The plurality of needles may be arranged in a line, or may be arranged in an array. The plurality of hair strands may include between 2-50 hair strands, the plurality of needles may include between 2-50 needles, the plurality of hair anchors may include between 2-50 self-expanding hair anchors, and the plurality of pushers may include between 2-50 pushers. Penetrating may occur at an angle orthogonal to or non-orthogonal to a surface of the skin. Expelling may occur simultaneously in response to force exerted on a plunger, or may occur in a staggered manner. The implantation depth may be substantially the same for each needle or may differ between needles. The plurality of needles may be movably contained within a housing that may be brought against the skin prior to implantation and removed from the skin after implantation. The hair strands may extend partially or fully through the plunger, and removing may include pulling the rest of the hair implantation assembly, without the hair strands and the hair anchors, away from the skin such that the hair strands slide through the plunger and the pushers upon removal leaving portions of the hair strands and the hair anchors embedded in the target tissue. Additional details of the method and technical details associated with the method are contained in the following description and are considered part of the methods of the invention.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

Technical elements of the foregoing summary are sometimes described in combination with other technical details as a short hand only. It is to be understood that inventive aspects are considered to lie in each individual technical detail, either alone or in combination with one or more other of the technical details. Thus, all permutations and combinations of elements described above are to be considered as within the scope of the invention.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIGS. 1 and 2 illustrate perspective views of a hair anchor, according to an exemplary embodiment of the present disclosure.

FIG. 3 illustrates a cross-sectional view of a hair anchor and a hair strand, according to an exemplary embodiment of the present disclosure.

DETAILED DESCRIPTION OF EXEMPLARY EMBODIMENTS

Figure 4:
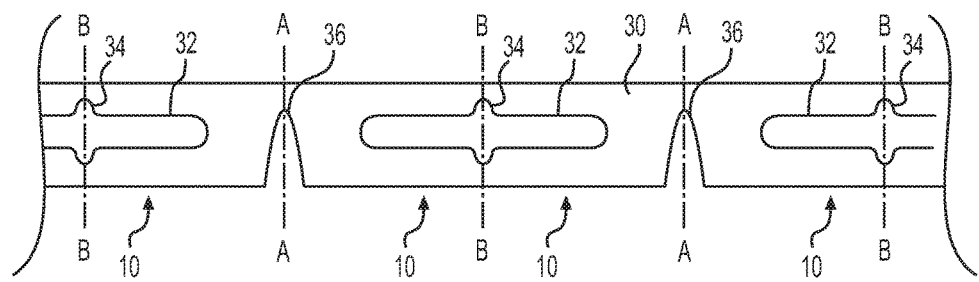
FIG. 4 illustrates a plan view of an elongated metal tube, according to an exemplary embodiment of the present disclosure.

Reference will now be made in detail to exemplary embodiments of the present disclosure, examples of which are illustrated in the accompanying drawings. Wherever possible, the same reference numbers will be used throughout the drawings to refer to the same or like parts.

Anchor Forming Process

Some embodiments of the present disclosure may include a hair anchor. As used herein, a hair anchor may include any structure that is capable of retaining one or more hair strands within target tissue of a subject individual. Each hair strand may include an implant end configured for implantation in the target tissue and a shaft configured to extend through the target tissue to a location external to the subject individual. The hair strands may be natural hair strands or synthetic hair strands. The hair strands may be substantially the same color, or alternatively, the hair strands may include two or more different colors. The target tissue may include any tissue, including but not limited to, tissue on the scalp or on the face (e.g., eyebrows).

A hair anchor may include a first portion that retains the hair strand and at least a second portion for securing the hair strand within the target tissue. In some embodiments, at least the second portion may be made out of resilient material, such that the second portion may flex in a desired manner.

In some embodiments, both the first portion and the second portion may be made of a resilient material. For example, the first and second portion may be made of a shape memory ahoy, such as, for example, Nitinol. The first and second portion may alternatively or additionally be made of other biocompatible materials, as desired. In the following description, the first portion may be characterized as an anchor body, an anchor body portion, or a hair holder portion, while the second portion may be characterized as a resilient member, a spring biased leaf, or a deployable leaf.

In some embodiments, the hair anchor may be self-expanding. For example, the hair anchor may have at least one portion that is capable of engaging with the target tissue or expanding upon implantation without the exertion of a deformation force at the time of implantation. For instance, the hair anchor may be pre-biased to expand and may expand once released from a sheath or other restrictive carrier. Alternatively, there may be other release mechanisms that permit the hair anchor to engage with or expand within the target tissue under a pre-biased force once released.

One example of a hair anchor in accordance with some embodiments of the present disclosure is hair anchor 10 illustrated in FIGS. 1-3. In some embodiments, hair anchor 10 may have an anchor body 12 at a first, implant end and at least one resilient member 14 connected to body 12 at a second, distal end opposite the first end. Body 12 may include a tube having an opening 16 configured to receive at least one hair strand 20, as shown in FIG. 3. Opening 16 may define a channel within the tube of body 12 through which hair strand 20 passes. In some embodiments, the tube of body 12 may have continuous, unperforated walls (i.e., without any slits disposed therein). Thus, hair strand 20 may pass through an entire length of body 12, and may be maintained axially along the length of body 12, without being permitted to deviate substantially from a longitudinal axis of body 12. For example, the absence of a slit in body 12 prevents hair strand 20 from laterally exiting body 12, ensuring that hair strand 20 exits through the channel of body 12. In some embodiments, as shown in FIG. 2, while hair anchor 10 is in a closed configuration, the edges of resilient members 14 may generally form an opening 18 through which haft strand 20 extends. This configuration may ensure hair strand 20 is maintained substantially along a longitudinal axis of hair anchor 10.

Resilient member 14 may be configured to flex in a direction away from a longitudinal axis of body 12 upon implantation into the target tissue to thereby resist removal of hair strand 20 from the target tissue when forces are exerted on hair strand 20 from a location external to the subject individual. In the embodiment shown in FIGS. 1-3, anchor 10 may have two resilient members 14. However, it is contemplated that anchor 10 may instead have any number of resilient members 14, as desired.

In accordance with some embodiments of the present disclosure, hair strand 20 may have an implant end configured for implantation in the target tissue of the subject individual and a shaft 24 configured to extend through the target tissue to a location external to the subject individual. As shown in FIG. 3, the implant end of hair strand 20 may include a nodule 22. As used herein, a nodule may include a bulge, a bulb, any structure having at least a partially bulbous shape, a protrusion, a deformation, a mass of rounded material, a regular or irregular shape, or any widening of an end of hair strand 20, regardless of its shape or size. Nodule 22 may be a contiguous structure extending directly from the surface of hair strand 20 itself (as opposed to being a fold or doubling over of the strand as would occur in a knot). In some, but not necessarily all, embodiments, the use of a physical widening or deformation of the strand itself, as opposed to a knot, may provide additional strength and may provide manufacturing benefits.

In the embodiment shown in FIG. 3, nodule 22 is illustrated as a bulbous shape for exemplary purposes only. However, it is contemplated that nodule 22 may alternatively include other shapes, such as polyhedrons, cylinders, cones, spheres, any portion of any of the forgoing, or any other shape, including random shapes.

In some embodiments, nodule 22 may be integrally formed with shaft 24 of hair strand 20. Nodule 22 may also have a width that is substantially greater than a width of shaft 24. Further, nodule 22 may have a width that is substantially greater than a diameter of opening 16, such that only shaft 24 can be threaded through the channel of body 12. In some embodiments, upon implantation in the target tissue, hair strand 20 may be maintained along a longitudinal axis of anchor 10.

In some embodiments, hair anchor 10 and hair strand 20 may be sized to allow proper implantation within the target tissue without causing infection or discomfort to the subject individual. For example, hair anchor 10 may have a total length of less than about 1 mm, in some embodiments, hair anchor 10 may have a length of about 0.3-1.0 mm. Hair anchor 10 may also have an opening that is no greater than about 1.5 times a width of hair strand 20. In one embodiment, opening 16 may have a diameter of about 0.07-0.18 mm. Further, an outer diameter of body 12 may be no greater than three times a diameter of hair strand 20. In one embodiment, the outer diameter of body 12 may be about 0.15-0.25 mm. On the other hand, shaft 24 of hair strand 20 may have a diameter of 0.05-0.15 mm, while nodule 22 may have a diameter of 0.15-0.26 mm. In some embodiments, hair anchor 10 may be made of a different material than hair strand 20. In some embodiments, hair anchor 10 may have a rigidity substantially greater than a rigidity of hair strand 20. Specifically, hair anchor 10 may be less flexible than hair strand 20.

A hair anchor consistent with embodiments of the present disclosure may be prepared by a process whereby a plurality of hair anchors are formed from a single elongated metal tube. Alternatively, each hair anchor may instead be cut individually, although this process can often be more difficult and time consuming due to the small size of each hair anchor. The metal tube may have a channel extending an entire length of the tube. The channel may correspond to the channel within each anchor body. The metal tube may be made of biocompatible material, such as, for example, Nitinol. One example of an elongated metal tube in accordance with some embodiments of the present disclosure is illustrated in FIG. 4 as metal tube 30.

In some embodiments of the present disclosure, the anchor forming process may include a step of forming at least two slits in an elongated direction of the elongated metal tube. As used herein, a slit may be any gap where material has been removed or two previously joined parts have been separated from each other. In some embodiments, each slit may span prospective end portions of at least two hair anchors. That is, at the time the slits are formed, the elongated metal tube may not yet have been severed. Thus, each slit may span portions that will ultimately become end portions of at least two hair anchors. By way of example, in FIGS. 4 and 5A, metal tube 30 may include a first slit 32 and a second slit 33. As shown in FIG. 4, the portion of slit 32 to the right of lines B-B will each become part of one hair anchor, while the portions of slit 32 to the left of lines B-B will each become part of other hair anchors.

Figure 5A:
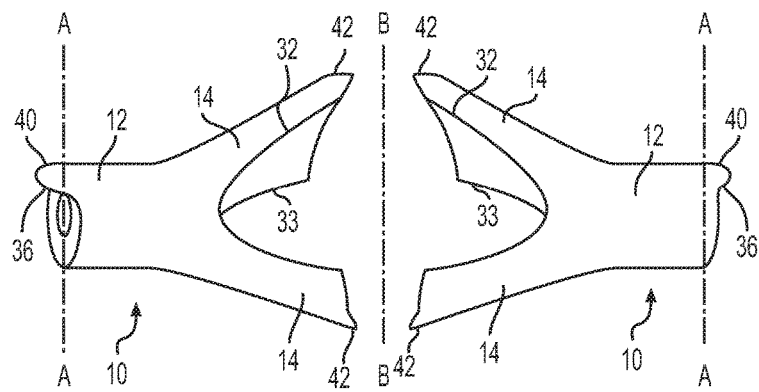
FIG. 5A illustrates a perspective view of separate hair anchors, according to an exemplary embodiment of the present disclosure.

In some embodiments, the at least two slits may cooperate to define at least two resilient members of a single hair anchor. By way of example, in FIG. 5A, the edges of slits 32 and 33 cooperate to each define a separate resilient member 14. The at least two resilient members may be integral with and extend from a tubular body portion of the hair anchor that is undissected by the at least two slits. For example, as illustrated in FIG. 5A, resilient members 14 integrally extend from body 12. As illustrated, slits 32 and 33 do not extend into body 12.

The plurality of hair anchors may be positioned such that at least two resilient members extend between two tubular body portions of two prospective hair anchors. For example, as illustrated in FIG. 4, due to the fact that the tube has not yet been severed into individual hair anchors, the portions of the tube on opposing sides of line B-B will each become part of a separate anchor. FIG. 4 and this description provide only one example of how a hair anchor may be formed, and it is contemplated that, consistent with the invention, hair anchors may be formed in other ways, and that the slits may be cut in numerous ways to form a similar shaped hair anchor.

The slits may be formed using any suitable cutting machine including, but not limited to, a laser cutting machine, a wire cutting machine, an electrical discharge machine, or a micro-milling machine. In some embodiments, an X-Y laser cutting machine or a rotating laser cutting machine may be used.

FIG. 4 illustrates one example of a slitted metal tube 30. Because FIG. 4 is a plan view, only one of each of three pairs of slits 32 is visible. The second of each pair of slits 33, is visible in the perspective view of FIG. 5A. Thus, in some embodiments, a first slit 32 may be cut in a wall of metal tube 30, and a second slit 33 (not shown in FIG. 4) may be cut in an opposing wall of metal tube 30. The first slit 32 may extend generally in a direction of a longitudinal axis of metal tube 30, while the second slit 33 may generally oppose the first slit 32. In some embodiments, the second slit 33 may be directly oppose and mirror the first slit 32. In other embodiments, the second slit 33 may not directly oppose and/or directly mirror the first slit 32. Slits 32, 33 may be formed in such a manner to facilitate severing metal tube 30 into a plurality of hair anchors 10. Such severing may be achieved, for example, by applying a bending moment between a hair anchor to be severed and a remaining portion of tube 30.

The process according to some embodiments of the present disclosure may further include a step of severing the elongated metal tube at an intermediate location along the at least two slits such that a first portion of each of the at least two slits is contained in one of the at least two hair anchors and a second portion of each of the at least two slits remains attached to the elongated metal tube for inclusion in a subsequent hair anchor to be later severed from the elongated metal tube. As used herein, severing may refer to cutting, splitting, separating, or breaking the elongated metal tube. Severing the elongated metal tube may also include applying force in opposing directions along the longitudinal axis of the metal tube to tear apart portions connecting adjacent hair anchors along each slit in the metal tube. The force may be applied by an operator, or alternatively, by machine. Severing the elongated metal tube may alternatively include cutting tube 30 along line B-B in FIG. 4. As long as one or more parts of the elongated metal tube are separated, the elongated metal tube is considered to have been severed.

Figure 5B:
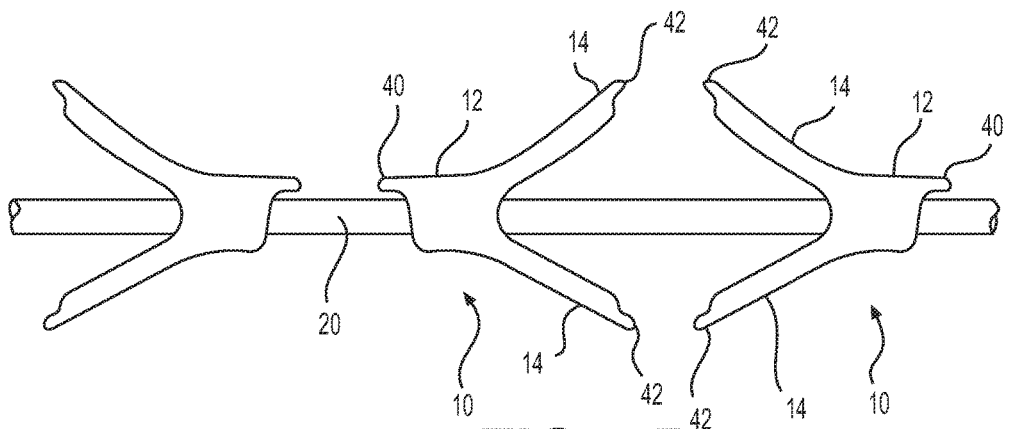
FIG. 5B illustrates a plan view of separate hair anchors and a strand of material, according to an exemplary embodiment of the present disclosure.

One example of an elongated metal tube 30 after being severed is illustrated in FIGS. 5A and 5B. As shown in FIG. 5A, metal tube 30 may be broken, cut, or otherwise severed along line B-B at the intermediate location along slits 32, 33. As shown in FIG. 5B, what was metal tube 30 is separated into a plurality of hair anchors 10 after being severed. The plurality of hair anchors 10 are shown spaced apart from each other as the result of forces applied in opposing directions along the longitudinal axis of metal tube 30. In some embodiments, each hair anchor 10 may individually be severed from metal tube 30. Alternatively, a plurality of hair anchors 10 may be severed from metal tube 30 simultaneously.

In some embodiments, to further facilitate severing the elongated metal tube, the process may further include forming a slot at the intermediate location along each slit. As used herein, a slot may include an aperture in the elongated metal tube and extending from the slit. The slot may be formed using a similar process as used in forming the slits. The slot may be configured to facilitate severing of the elongated metal tube at an intermediate location along the at least two slits. Specifically, the slot may be designed to form a weakened area in the elongated metal tube, such that, with sufficient force, adjacent hair anchors may be separated. It is contemplated, however, that the slot may not be required to sever the elongated metal tube.

As shown in FIG. 4, metal tube 30 may include a slot 34 formed at the intermediate location along slit 32. In some embodiments, a first slot 34 may be cut in a wall of metal tube 30, and a second slot (not shown in FIG. 4) may be cut in an opposing wall of metal tube 30. The slot 34 may extend generally in a direction transverse to the longitudinal axis of metal tube 30. The second slot (not shown in FIG. 4) may or may not mirror the first slot 34. In other embodiments, a single slot 34 may be formed on only one side of metal tube 30. As shown in FIG. 5A, metal tube 30 may be severed along line B-B at the location of slot 34, thereby forming a plurality of separated hair anchors 10 shown in FIG. 5B.

In some embodiments, to further facilitate severing the elongated metal tube, the process may further include forming a notch between two adjacent tubular body portions. As used herein, a notch may include an indentation or incision on an edge or surface of the elongated metal tube. The notch may be formed using a similar process as used in forming the slits and/or the slots. The notch may be configured to facilitate severing of the elongated metal tube at a location between the two adjacent tubular body portions. In some embodiments, there may be a gap of about twice the length of a hair anchor between adjacent notches prior to severing.

An example of a notch 36 is illustrated in FIG. 4, where notch 36 in metal tube 30 is located between two adjacent tubular body portions (e.g., bodies 12 shown in FIGS. 1-3). Notch 36 may be cut in a wall of metal tube 30, such that notch 36 may extend generally in a direction transverse to the longitudinal axis of metal tube 30. In some embodiments, a plurality of notches 36 may be cut into the tube wall. As shown in FIG. 5A, metal tube 30 may be severed along line A-A along to form the plurality of separated hair anchors 10 shown in FIG. 5B.

In some embodiments in accordance with the present disclosure, the process may further include a step of inserting a hair strand into the metal tube. As used herein, inserting may include threading, placing, or introducing the hair strand into the metal tube either manually and/or automatically via one or more machines. The inserted hair strand may be the hair strand to be later implanted into the target tissue. Alternatively, the inserted hair strand may be used as a place holder to allow the hair anchor to be properly sized around the hair strand. In some embodiments, the inserted hair strand may be an individual hair strand to be associated with one hair anchor. Or, alternatively, the hair strand may be one hair strand associated with a plurality of hair anchors that will be later cut for each individual hair anchor.

As shown in FIG. 5B, hair strand 20 may be inserted into the channel associated with metal tube 30. In some embodiments, the insertion of hair strand 20 may occur prior to severing the metal tube 30. Alternatively, each hair strand 20 may be inserted into each hair anchor 10 after metal tube 30 has been severed.

In some embodiments in accordance with the present disclosure, the process may further include a step of deforming the resilient member to cause the resilient member to diverge from a longitudinal axis of the metal tube. As used herein, deforming may include any form of bending, twisting, or applying force to the resilient member. Deforming may also include applying a heat treatment to the resilient member.

As shown in FIGS. 5A and 5B, metal tube 30 may be deformed such that resilient members 14 of each hair anchor 10 diverge from the longitudinal axis of metal tube 30. In some embodiments, the deformation may occur prior to severing hair anchor 10 from metal tube 30. Alternatively, each hair anchor 10 may be deformed after metal tube 30 has been severed.

Formation of Burrs

As a result of the anchor forming process described above, some embodiments in accordance with the present disclosure may include a burr that is formed on the hair anchor. As used herein, a burr may be a rough area or remnant on the hair anchor that is left after the metal tube is cut or otherwise severed. A burr may, for example, protrude out from the hair anchor. The formation of the burr may occur when multiple hair anchors are formed together as part of the metal tube, and are then separated from each other. Thus, the inclusion of burrs may facilitate a large scale manufacturing process.

In some embodiments, there may be more than one burr connected to the hair anchor at different locations. For example, there may be at least one burr connected to an anchor body of the hair anchor. Alternatively or additionally, there may be at least one additional burr connected to one or more resilient members of the hair anchor. Each burr may be integrally formed with the corresponding hair anchor part.

As shown in FIGS. 5A and 5B, a plurality of exemplary disclosed hair anchors 10 may be separated after being severed from metal tube 30. For example, a first burr 40 may be attached to body 12 of hair anchor 10. Burr 40 may be located on only one side surface of body 12 as a result of severing metal tube 30 along line A-A at notch 36. Thus, when metal tube 30 is severed at notch 36, a portion of notch 36 may remain intact with body 12 of one hair anchor 10, while another portion of notch 36 may remain intact with body 12 of another hair anchor 10. This is only one example based on the anchor configuration of FIGS. 5A and 5B, and it is contemplated that burr 40 may be located at a different position on body 12, depending on a position of notch 36. Further, burr 40 may also vary in size depending on a size of notch 36.

In some embodiments, a second burr 42 may be attached to at least one resilient member 14 of hair anchor 10, as shown in FIGS. 5A and 5B. In one embodiment, second burr 42 may be located on each resilient member 14. However, in other embodiments, second burr 42 may be only located on only one of two resilient members 14.

In some embodiments, burr 42 may be formed on resilient members 14 when metal tube 30 is severed along line B-B at slots 34 or at the intermediate location along slits 32. For example, when metal tube 30 is severed at slot 34, a portion of slot 34 may remain intact with resilient member 14 of one hair anchor 10, while another portion of slot 34 may remain intact with resilient member 14 of another hair anchor 10. In some embodiments, burr 42 may be located on a distal end of resilient member 14. However, the location of burr 42 on resilient member 14 may vary, depending on a position of slot 34. Further, burr 42 may also vary in size depending on a size of slot 34.

In some embodiments in accordance with the present disclosure, burrs 40, 42 may remain intact with hair anchor 10 during implantation. In addition, burrs 40, 42 may further aid in securing the hair anchor within the target tissue. In other embodiments, burrs 40, 42 may be removed from hair anchors 10 using one or more material removal processes, such as, for example, cutting or grinding.

Nodule Forming Process

Some embodiments in accordance with the present disclosure may be directed to a process of forming a nodule on an end of a hair strand by treating the hair strand. The nodule forming process may be performed either before or after the anchor forming process described above. In some embodiments, the nodule may be formed on the implant end of a hair strand. The nodule may have a width greater than a width of the remaining portion of the hair strand (e.g., the shaft of the hair strand). The width of the nodule may ensure that the hair strand remains secured to an associated hair anchor after implantation in the target tissue.

Figure 6:
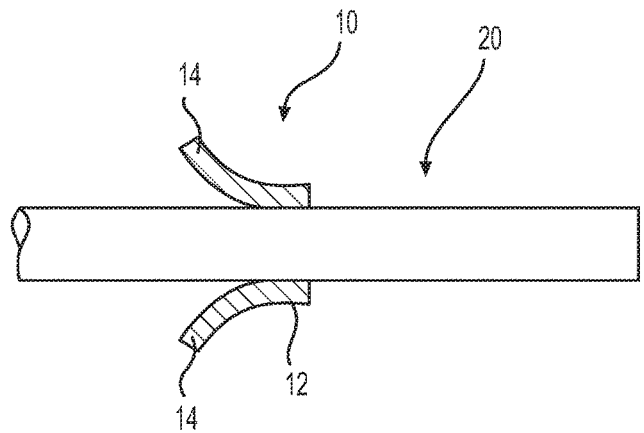
FIGS. 6, 7, and 8A illustrate a plan view of a hair anchor and a hair strand subject to a treatment, according to an exemplary embodiment of the present disclosure.
Figure 7:
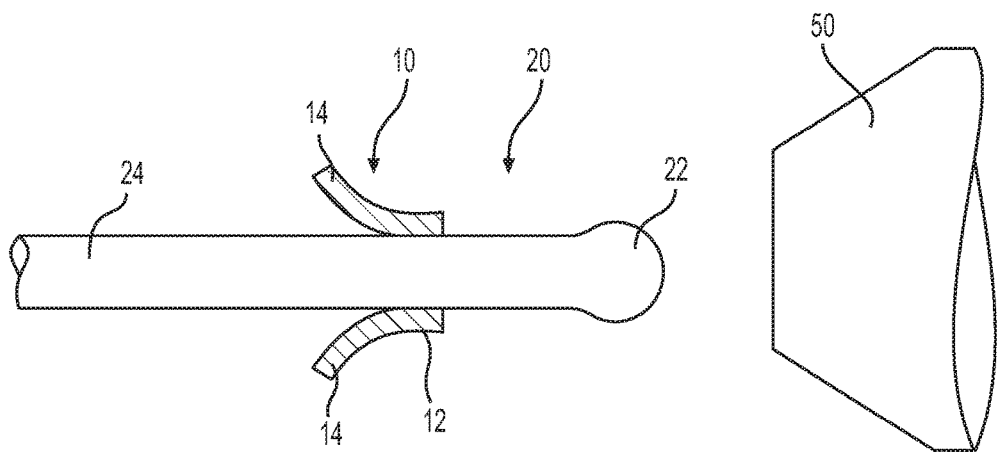
Figure 8A:
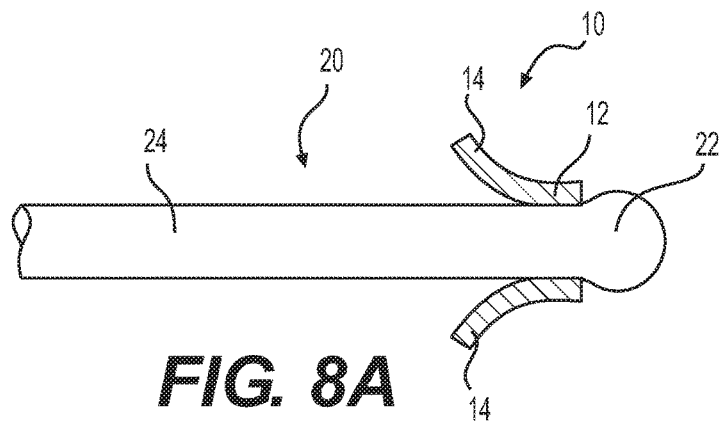
Figure 8B:
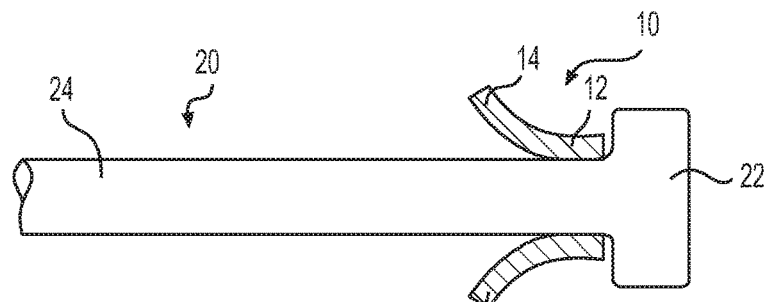
FIGS. 8B-8E illustrate plan views of hair anchors and hair strands subject to different treatments, according to other exemplary embodiments of the present disclosure.
Figure 8C:
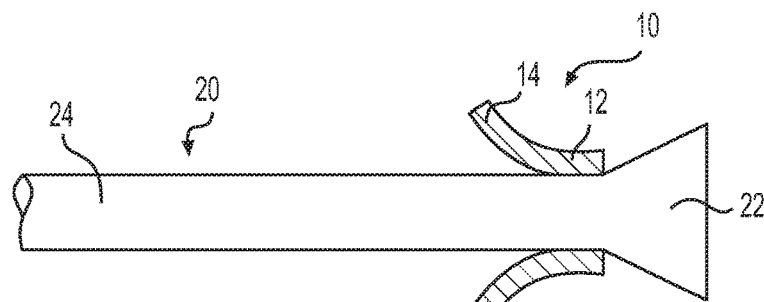
Figure 8D:
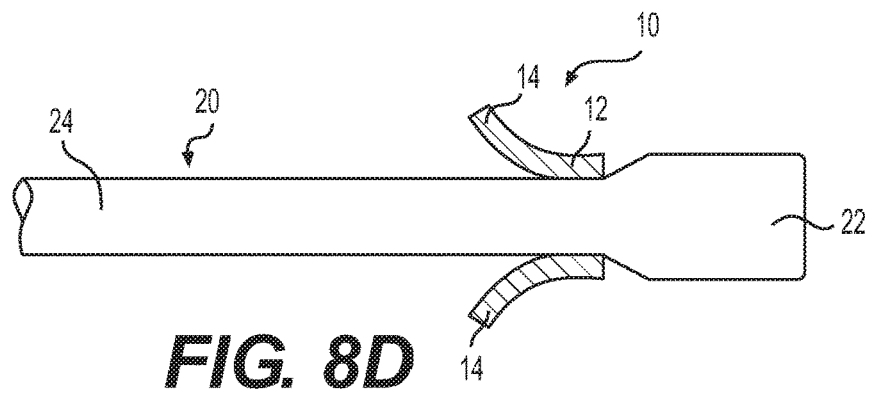
Figure 8E:
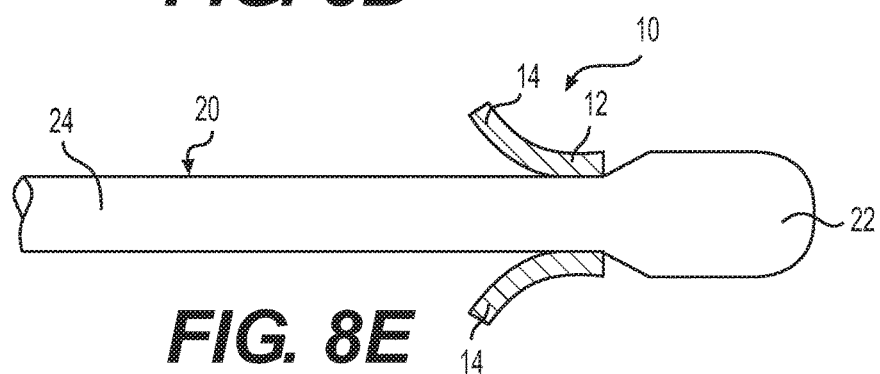

In some embodiments, the nodule forming process may include a step of obtaining a strand of material for use in a hair implant procedure. As used herein, obtaining may include purchasing, acquiring, securing, or using the strand of material. It is contemplated that, as long as the strand of material is made available for use in the nodule forming process, the strand of material may be considered to have been obtained. The strand of material may be made of natural hair or synthetic hair. In some embodiments, the strand of material may be an individual hair strand to be associated with a single hair anchor. Or, alternatively, the strand of material may be a single hair strand to be threaded through a plurality of interconnected hair anchors that will be later separated. FIGS. 6, 7, and 8A illustrate one example of a portion of a strand of material, which is used to form hair strand 20.

In some embodiments, the process may further include subjecting an end of the hair strand to a treatment in order to cause a nodule on the end of the hair strand. The treatment may include one or more procedures of heating, bonding, coating, or chemically treating the hair strand. For example, the treatment may include any heat treatment process that causes the hair strand to deform and create the nodule on the end of the hair strand. In one embodiment, the end of the hair strand may be heated to a temperature above a melting temperature ($T_m$) of the material comprising the hair strand, causing the hair strand to melt and deform to form the nodule. In another embodiment, the end of the hair strand may be heated to a temperature above a glass transition temperature ($T_g$) of the material comprising the hair strand but below the melting temperature, causing the hair strand to soften. The heating may then be followed by an application of force to the heated region, causing the molecules in the material to slide against each other and form the nodule on the end of the hair strand. In yet another embodiment, the end of the hair strand may be bonded with an additional strand of material, such as, for example, a separate nodule via an adhesive. For example, a shaft of a hair strand and a nodule of a hair strand may initially be separate components that are later bonded together to form a completed hair strand. In other embodiments, the end of hair strand may be subject to one or more chemical agents, causing deformation to the end of the hair strand.

FIG. 7 illustrates one example of a treatment of hair strand 20. As shown in FIG. 7, an end of hair strand 20 may be subject to heat treatment using a heating device 50. Heating device 50 may include any mechanism capable of causing heat (e.g., electric, gas, chemical, etc.). In one embodiment, as illustrated in FIG. 7, heating device 50 may be spaced from the end of hair strand 20 to heat the end of hair strand 20 to a temperature above the melting temperature of hair strand 20. In another embodiment, heating device 50 may be pressed against the end of hair strand 20 to heat the end of hair strand 20 to a temperature above the glass transition temperature of hair strand 20 and apply force to hair strand 20. In both embodiments, a nodule 22 may be formed on the implant end of hair strand 20. Nodule 22 may be formed such that the implant end has a greater width than the rest of hair strand 20 (i.e., shaft 24).

The nodule may take the shape of a bulb, a bead, a sphere, or any other desired shape depending on the process used to form the nodule. For example, if heating device 50 or another structure is pressed against the end of hair strand 20, nodule 22 may be influenced by the shape of the pressing structure. Thus, the structure that presses against the implant end may include a die to allow nodule 22 to be formed to a desired shape.

As shown in FIG. 8A, nodule 22 may be bulbous in one embodiment. However, as shown in FIGS. 8B-8E, nodule 22 may take many different shapes. For example, nodule 22 may be shaped like a rectangular prism (shown in FIG. 8B), a triangular prism (shown in FIG. 8C), a pentagonal prism (shown in FIG. 8D), or an ellipsoid (shown in FIG. 8E).

The size of the nodule may also vary depending on the process used to form the nodule. For example, the duration of heating or the size of the structure pressed against the end of hair strand 20 may affect the size of nodule 22. In some embodiments, nodule 22 may be large enough to inhibit the implant end from passing through opening 16 of hair anchor 10, but small enough to fit comfortably within the target tissue of the subject individual.

In some embodiments, the process may further include threading the hair strand through a hair anchor. As used herein, threading may include inserting, placing, or introducing the hair strand through the hair anchor either manually and/or automatically via one or more machines. In some embodiments, the hair strand may be inserted into the hair anchor before treatment of the hair strand. Alternatively, however, the hair strand may first be treated and then inserted into the hair anchor.

In some embodiments, the hair strand may be bonded to the hair anchor using an adhesive. Alternatively or additionally, the hair strand may be mechanically connected to the hair anchor. For example, the hair anchor may have a channel extending therethrough and a channel opening with a width smaller than the width of the nodule on the end of the hair strand to thereby inhibit the implant end from being pulled through the opening. As a result, the hair strand may be secured to the hair anchor when external forces are applied to the hair strand after implantation.

FIGS. 6, 7, and 8A illustrate one example of a hair strand 20 with a hair anchor 10 that is assembled over hair strand 20 prior to treatment of hair strand 20. However, hair anchor 10 may alternatively be placed over hair strand 20 after treatment of hair strand 20. As shown in FIG. 8A, after treatment of hair strand 20 and formation of nodule 22, hair anchor 10 may be moved to abut against nodule 22 and to secure hair strand 20 to hair anchor 10.

In some embodiments, hair anchor 10 and/or a portion of hair strand 20 may be coated with Paraylene. The Paraylene coating may help to secure hair strand 20 and hair anchor 10 together, while also protecting in the subject individual from discomfort caused by sharp edges and rough surfaces of either hair anchor 10 or hair strand 20. In one embodiment, hair anchor 10 and nodule 22 may be coated with Paraylene. In another embodiment, only hair anchor 10, or only part of hair strand 20 may be coated with Paraylene.

Crystalline/Orientation Structure of Synthetic Hair

As a result of the nodule forming process described above, some embodiments in accordance with the present disclosure may include a synthetic hair having a nodule with a different crystalline and/or orientation structure than that of the shaft. As used herein, a synthetic hair may be a strand of material that is manufactured with properties similar to a natural human hair. The synthetic hair may have substantially the same size, weight, and/or texture of a natural human hair. Alternatively, the properties of the synthetic hair may significantly differ from that of a human hair.

Figure 9:
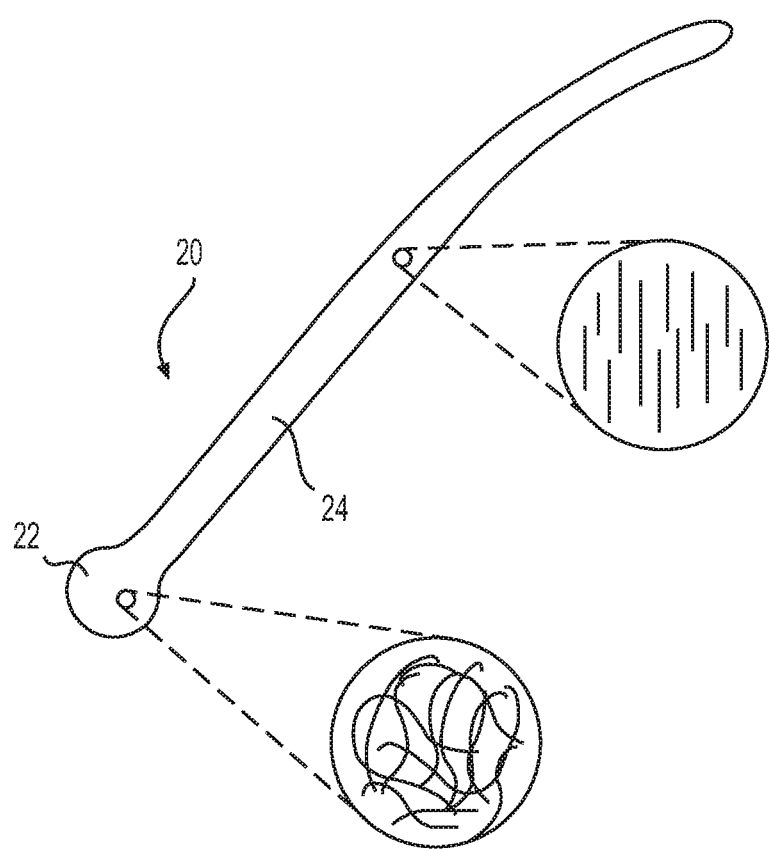
FIG. 9 illustrates a schematic view of a synthetic hair, according to an exemplary embodiment of the present disclosure.

In some embodiments, the synthetic hair may be made of monofilament or multi-filament synthetic materials. In some embodiments, the synthetic hair may include, for example, polyamides, polyimides, polyethylene terephthalate (PET), polybutylene terephtalate (PBT) or similar materials. The synthetic hair may also be coated with additional antibiotic materials. In addition, the synthetic hair may be pre-colored, for example, with commercially available hair dyes. In some embodiments, coloring pigments, including inorganic pigments, may be added to a polymer based synthetic hair during processing. FIG. 9 illustrates one example of a synthetic hair that is used to form hair strand 20.

In some embodiments, the synthetic hair may have one or more crystalline and/or orientation structures. As used herein, a crystalline structure may refer to any unique arrangement of atoms, ions, or molecules in a crystalline liquid or solid. Normally, the crystallinity level of a polymer is correlated with its orientation level, thus in some embodiments, a crystalline structure of a synthetic hair may refer to an orientation of molecules within the synthetic hair. For example, synthetic hairs with a higher percentage of aligned molecules may have a higher crystalline structure level.

As shown in FIG. 9, shaft 24 of hair strand 20 may have a first crystalline/orientation structure level, while nodule 22 may have a second crystalline/orientation structure level that is substantially different than the first crystalline structure level. In particular, the molecules in shaft 24 may be aligned generally in a longitudinal direction of shaft 24, while the molecules in nodule 22 may be generally unaligned with the longitudinal axis of shaft 24. This disparity in crystalline/orientation structure may be a result of nodule 22 being formed through heat treating the distal end portion of shaft 24. For example, while the molecules along shaft 24 may remain at their original orientation, the molecules in nodule 22 that were affected by the heat during formation of the nodule may become more amorphous in their orientation. As a result, the crystalline structure level of shaft 24 may be greater than the crystalline structure level of nodule 22. In some embodiments, a crystalline structure level in shaft 24 may be at least 30% higher than a crystalline structure level in nodule 22. In one embodiment, a crystalline structure level in shaft 24 may be approximately 50% higher than a crystalline structure level in nodule 22.

As a result of shaft 24 having a higher crystalline structure level, in some embodiments, shaft 24 may have a higher percent of aligned molecules than a percentage of aligned molecules in nodule 22. Shaft 24 may also have a higher transparency than a transparency of nodule 22. Further, shaft 24 may also have molecules with a higher molecule weight than modules within nodule 22. Shaft 24 may further have a tensile strength that is greater than a tensile strength of nodule 22.

In some embodiments in accordance with the present disclosure, shaft 24 may have a tear force that is greater than a shaft of a normal human hair. As used herein, a tear force may refer to a measurement of how well a material can withstand the effects of tearing. A tear force may be measured in terms of grams, which represents the amount of mass, subject to gravitational forces, that is required to tear a material. In some embodiments, shaft 24 may have a tear force that is greater than 300 grams. In other embodiments, shaft 24 may have a tear force that is greater than 500 grams. In yet additional embodiments, shaft 24 may have a tear force that is between 300 and 700 grams.

Anchor Delivery Process

Figure 10:
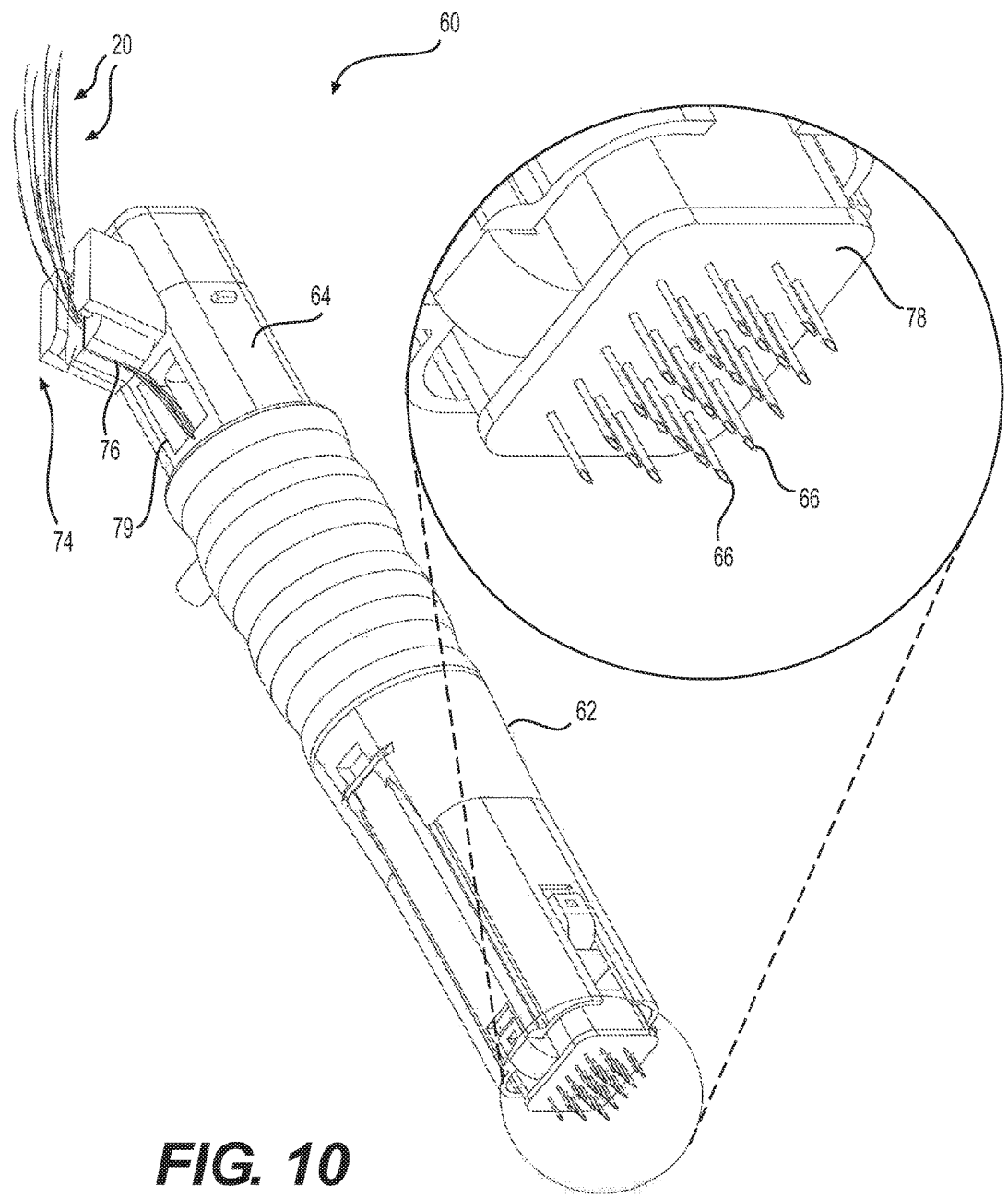
FIG. 10 illustrates a perspective view of a hair implantation assembly, according to an exemplary embodiment of the present disclosure.

Some embodiments in accordance with the present disclosure may include a hair implantation assembly. A hair implantation assembly may include one or more hair strands and/or hair anchors in accordance with embodiments described above. A hair implantation assembly may also include a mechanism for implanting the one or more hair strands and/or hair anchors into the target tissue. FIG. 10 illustrates one example of a hair implantation assembly 60.

In some embodiments, the mechanism may include a plurality of needles arranged in an array. An array can be any arrangement of needles in either one or two dimensions. For example, a row of needles may constitute an array, an arrangement of needles in rows and columns may constitute an array, or an arrangement of needles in any other pattern or in a random manner may constitute an array.

Each needle may include a hollow metal tube extending towards a distal end to form a needle tip. Each needle tip may have a piercing edge configured to cut at an angle enabling skin penetration when axial forces are applied to its corresponding needle. Each needle may define a bore, also known as a lumen. Each lumen may contain a single hair anchor in a manner that compresses at least one resilient member associated with the hair anchor toward an insertion axis of a corresponding lumen. The insertion axis may refer to a longitudinal axis of the lumen of each needle.

The hair implantation assembly may also include a plurality of pushers associated with the plurality of lumens. As used herein, a pusher may be any device capable of expelling an associated hair anchor from within its corresponding lumen into the target tissue. In some embodiments, a plurality of pushers may be configured to simultaneously expel a plurality of hair anchors into the target tissue. In some embodiments, the plurality of lumens and the plurality of pushers may be configured to cooperate to cause the plurality of resilient members to simultaneously move away from the insertion axis of each lumen when expelled into the target tissue. Each of the plurality of hair strands may be threaded through a corresponding pusher in order to prevent damage to the hair strands while implanting a plurality of hair strands simultaneously.

It is contemplated that, in other embodiments, less than all of the plurality of hair anchors may be expelled simultaneously. For example, in some embodiments, the plurality of hair anchors may be expelled sequentially. Or, alternatively, the plurality of hair anchors may be expelled in groups. In some embodiments, the plurality of hair anchors may be expelled at staggered times in response to a continuous expulsion force during a single implantation procedure. The plurality of hair anchors may also be subject to staggered expulsions upon exertion of sequential forces.

Figure 12:
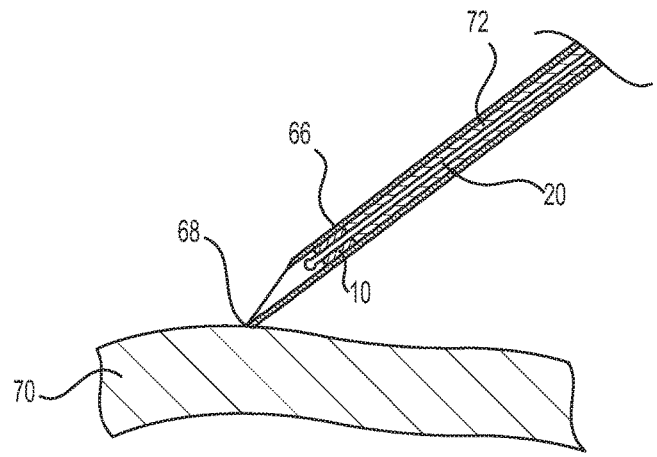
FIG. 12 illustrates a cross-sectional view of a portion of a hair implantation assembly, according to an exemplary embodiment of the present disclosure.

As shown in FIG. 10, an exemplary hair implantation assembly 60 may include a plurality of needles 66. As shown in FIG. 12, each needle 66 may have an associated needle tip 68 configured to puncture target tissue 70 and an associated pusher 72 configured to expel hair anchor 10 and hair strand 20 into target tissue 70. As shown in FIG. 12, pusher 72 may include a hollow tube defining a channel through which hair strand 20 passes and extends through an entire length of the tube. In some embodiments, needle 66 may have an outer diameter of about 0.24-0.40 mm and an inner diameter of 0.16-0.26 mm. Also, in some embodiments, pusher 72 may have an outer diameter of about 0.15-0.25 mm and an inner diameter of about 0.07-0.18 mm.

In one exemplary embodiment, prior to implantation, each needle 66 may contain a single hair strand 20 and a single hair anchor 10 in a manner that compresses two resilient members 14 associated with hair anchor 10 toward an insertion axis of a corresponding needle 66 (i.e., to a first position shown in FIG. 1). During implantation, the plurality of needles 66 and the plurality of pushers 68 may then cooperate to cause the plurality of resilient members 14 to simultaneously move away from the insertion axis of each needle 66 when expelled into the target tissue (i.e., to a second position shown in FIG. 2).

In the embodiment shown in FIG. 10, hair implantation assembly 60 may include at least 25 lumens, 25 pushers, 25 self-expanding hair anchors, and 25 hair strands. However, in another embodiment, hair implantation assembly 60 may include at least 35 lumens, 35 pushers, 35 self-expanding hair anchors, and 35 hair strands. In yet another embodiment, hair implantation assembly 60 may include at least 45 lumens, 45 pushers, 45 self-expanding hair anchors, and 45 hair strands. In still another embodiment, hair implantation assembly 60 may include greater than 50 lumens, 50 pushers, 50 self-expanding hair anchors, and 50 hair strands. In other embodiments, hair implantation assembly 60 may include fewer lumens, pushers, self-expanding hair anchors, and hair strands. For example, in one embodiment, hair implantation assembly 60 may include at least 2 lumens, 2 pushers, 2 self-expanding hair anchors, and 2 hair strands. In another embodiment, hair implantation assembly 60 may include at least 5 lumens, 5 pushers, 5 self-expanding hair anchors, and 5 hair strands. In yet another embodiment, hair implantation assembly 60 may include at least 12 lumens, 12 pushers, 12 self-expanding hair anchors, and 12 hair strands.

In some embodiments, the hair implantation assembly may also include a housing and a plunger contained within the housing. The housing may include an external casing configured to at least partially house the plunger, the pushers, and the needles. The plunger may include a deployment mechanism for transferring a deployment force simultaneously to each of the plurality of pushers. In some embodiments, the plunger may be configured to simultaneously convey an anchor expulsion force to each hair anchor within the plurality of needles.

As shown in FIG. 10, hair implantation assembly 60 may include a housing 62 and a plunger 64. Plunger 64 may have a centrally located bore in which a plurality of hair strands 20 are threaded internal to plunger 64. Plunger 64 may also have a side opening 79 through which the plurality of hair strands 20 are threaded external to plunger 64. In some embodiments, the plurality of hair strands 20 may pass through side opening 79 in a bundle. Alternatively, in other embodiments, the plurality of hair strands 20 may be unbundled, or instead, be bundled in groups of hair strands 20.

In some embodiments, a hair holder may be provided to hold the plurality of hair strands and prevent them from sliding out of the needles prior to the implantation (e.g. when the cartridge is held vertically or due to vibration during transportation). The hair holder may include any device capable of grasping, retaining, or securing one or more hair strands. The hair holder may ensure that the plurality of hair strands do not slide out of the needles before implantation. The hair holder may also reduce tangling of the plurality of hair strands during the implanting procedure.

For example, as shown in FIG. 10, hair implantation assembly 60 may include one exemplary disclosed hair holder 74 configured to secure a bundle of hair strands 20. In particular, hair holder 74 may have a slit 76 configured to hold hair strand 20 and apply friction to hair strands 20 to resist sliding out of needles 66 before implantation. In some embodiments, hair holder 74 may be made of a rubber material or other polymer, such as, for example, silicon.

Some embodiments in accordance with the present disclosure may be directed to a hair implantation assembly that orients the cuts of all the needles at a substantially common angle and arranges the needles with similar rotational orientations. For example, in some embodiments, each needle tip in the hair implantation assembly may be formed with a piercing edge on the needle tip at a circumferential position on each needle. The needles may also be arranged such that the piercing edge on each needle is located at a substantially common rotational orientation with respect to the piercing edge of each other needle. As a result, the plurality of hair strands may be implanted into the target tissue at a substantially common angle and be arranged within the target tissue in a substantially similar manner. In some embodiments, a support structure may be configured to hold the needles in the arranged manner. Such a configuration may allow an array of needles to simultaneously puncture the skin in a manner that is smoother and less traumatic for the subject individual. Such a configuration may also simplify the process of loading the needles with the hair anchors and hair strands.

For example, as shown in FIG. 10, hair implantation assembly 60 may be provided with needles 66 arranged at a substantially common angle. Needles 66 may also be arranged with substantially similar rotational orientations. Hair implantation assembly 60 may also include a support structure 78 that is configured to hold needles 66 such that the piercing edge on each needle 66 is located at a substantially common rotational orientation with respect to the piercing edge of each other needle 66. For example, support structure 78 may have plurality of openings through which needles 66 are configured to pass.

As shown in FIG. 12, when needles 66 are arranged at an angle with respect to target tissue 70, needles 66 may be oriented in a manner that allows needles 66 to puncture the skin in a less traumatic way. For example, in one embodiment, a beveled portion of needle tip 68 may be oriented in a direction away from target tissue 70. If instead the beveled portion of needle tip 68 were oriented in a direction facing target tissue 70, this would cause a higher penetration force, thereby resulting in more trauma for the subject individual.

Some embodiments of the present disclosure may be directed to hair implantation assembly that implants a row of hairs along a line. The hair implantation assembly may include a plurality of needles spaced from each other substantially in a line. Each of the plurality of needles may include a needle tip that is cut at an angle enabling skin penetration when an axial force is applied thereto. The hair implantation assembly may also include a plurality of pushers associated with the plurality of needles and configured to expel a plurality of hair anchors in a row, substantially along a line.

Figure 11:
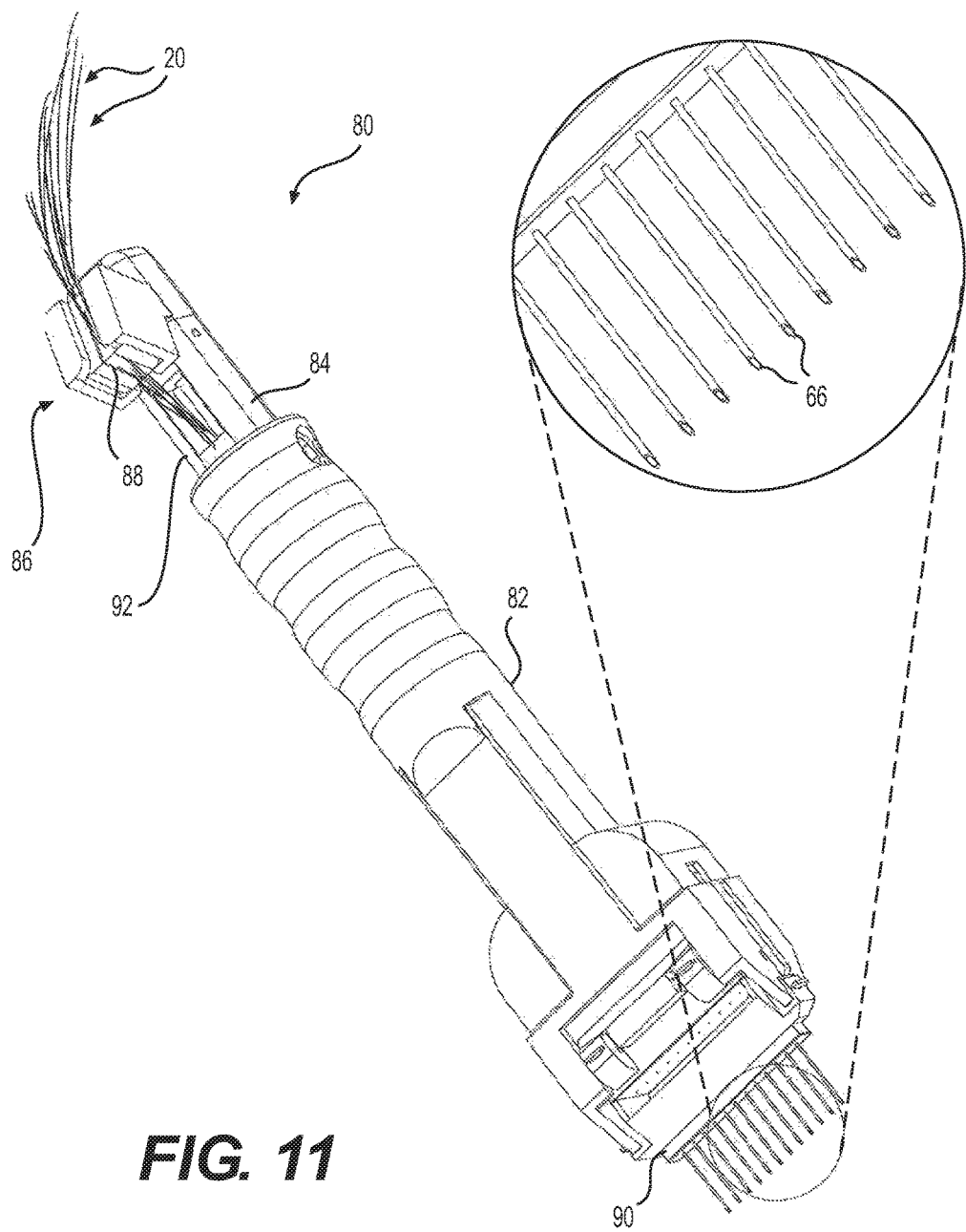
FIG. 11 illustrates a perspective view of another hair implantation assembly, according to an exemplary embodiment of the present disclosure.

FIG. 11 illustrates one example of a hair implantation assembly 80 that implants rows of hair strands 20 along at least one line. Like hair implantation assembly 60, hair implantation assembly 80 may include a plurality of needles 66, a housing 82, a plunger 84, a hair holder 86, a slit 88 associated with hair holder 86, a support structure 90, and an opening 92. However, unlike hair implantation assembly 60, hair implantation assembly 80 may include a single line of needles 66. This configuration may allow the operator to simultaneously implant hair strands 20 angularly to the same depth in the target tissue.

In some embodiments, needles 66 of hair implantation assembly 80 may be arranged in a single-file row. However, in other embodiments, there may be two or more lines of needles 66. Additionally, in one embodiment, the line of needles 66 may be substantially straight, while in another embodiment, the line of needles 66 may be curved.

Some embodiments of the present disclosure may be, directed to a hair implantation assembly for inserting hair strands into target tissue at a non-90 degree angle with respect to a surface of the target tissue. In order to achieve a non-90 degree angle, the hair implantation assembly may orient a plurality of needles transverse to a surface of the skin. This orientation may allow for traversed penetration to improve implanting in certain areas, such as, for example, the eyebrow regions.

Figure 13:
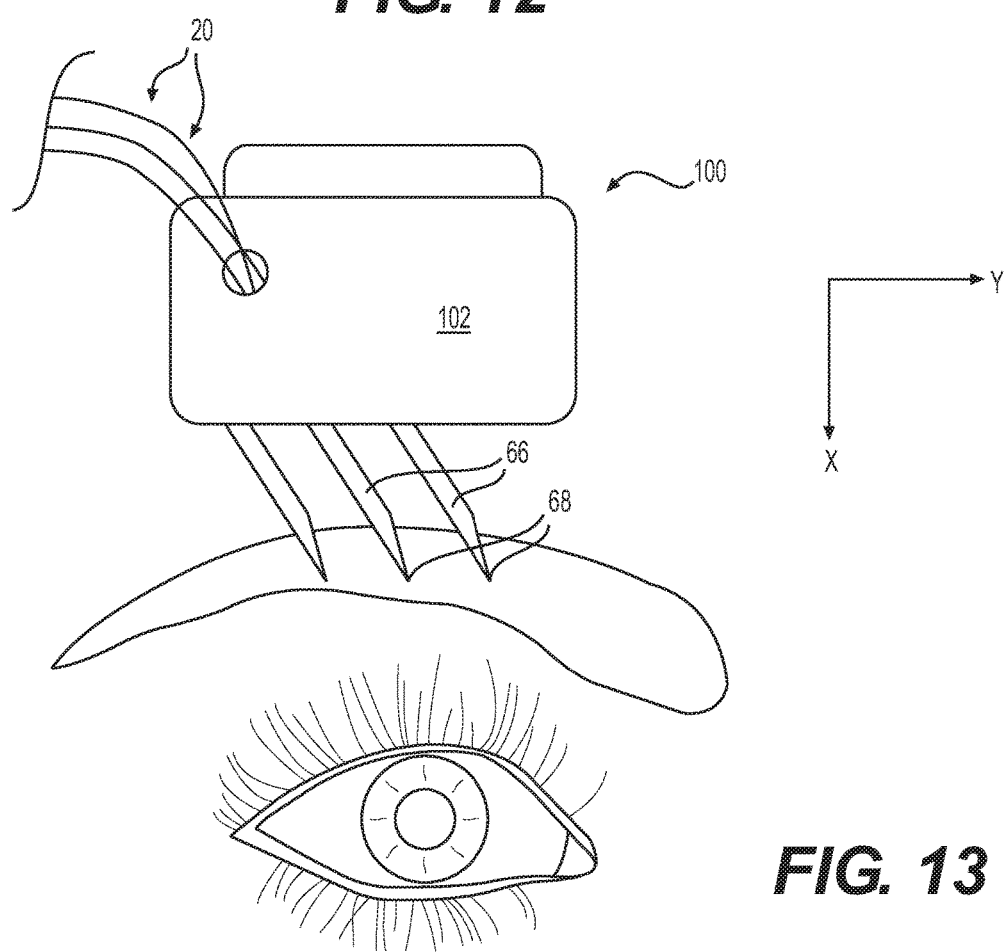
FIG. 13 illustrates a perspective view of yet another hair implantation assembly, according to an exemplary embodiment of the present disclosure.

FIG. 13 illustrates one example of a hair implantation assembly 100 for inserting hair strands into target tissue at a non-90 degree angle with respect to a surface of the target tissue. As shown in FIG. 13, hair implantation assembly 100 may be used on an eyebrow region of a subject individual. Hair implantation assembly 100 may include a contact surface 102 configured to rest against skin above the eyebrows of the subject individual. While resting against the skin, contact surface 102 may orient needles 66 at a substantially common non-90 degree angle with respect to contact surface 102. As a result, needle tips 68 may enter the target tissue at an angle transverse to a surface of the skin. This may cause the plurality of hair strands 20 to extend from the surface of the target tissue at the substantially common non-90 degree angle. In some embodiments, the substantially common non-90 degree angle may be measured with respect to a bottom of a housing of hair implantation assembly 100.

Some methods of the present disclosure may be directed to a method for hair implantation. The method may be performed using any of hair implantation assemblies 60, 80, and 100 described above. One exemplary method is described below using hair implantation assembly 60 and referring to FIGS. 10 and 12.

The method may include positioning needles 66 over a hair implantation site (e.g., a site where target tissue 70 is located). The method may further include penetrating skin of the implantation site with needles 66 along a penetration axis associated with each needle 66 such that each needle 66 reaches an implantation depth. Penetrating may occur at an angle orthogonal to or non-orthogonal to a surface of the skin. The implantation depth may be substantially the same for each needle 66 or may differ between needles 66. The method may further include expelling from each of needles 66 at the implantation depth, a hair anchor 10 and an associated hair strand 20 such that upon expulsion at least one resilient member 14 of each hair anchor 10 moves away from the penetration axis to secure each hair anchor 10 to target tissue 70. Expelling may occur simultaneously in response to force exerted on plunger 64, or may occur in a staggered manner.

In some embodiments, needles 66 may be movably contained within housing 62 that is brought against the skin prior to implantation and removed from the skin after implantation. Hair strands 20 may extend partially or fully through plunger 64. Removing may include pulling the rest of hair implantation assembly 60, without hair strands 20 and the hair anchors 10, away from the skin such that haft strands 20 slide through plunger 64 and pushers 72 upon removal leaving portions of the hair strands 20 and the hair anchors 10 embedded in target tissue 70.

Other embodiments of the present disclosure will be apparent to those skilled in the art from consideration of the specification and practice of the present disclosure.

While this disclosure provides examples of hair implant devices employed for the treatment of certain conditions, usage of the disclosed hair implant devices is not limited to the disclosed examples. The disclosure of uses of embodiments of the invention for hair implantation are to be considered exemplary only. In its broadest sense, the invention may be used in connection with the treatment of hair loss. Alternative embodiments will become apparent to those skilled in the art to which the present invention pertains without departing from its spirit and scope. Accordingly, the scope of the present invention is defined by the appended claims rather than the foregoing description.

What is claimed is:

1. A process of forming a plurality of hair anchors from a single elongated metal tube, the process comprising:
   forming at least two slits in an elongated direction of the elongated metal tube, each slit spanning prospective end portions of at least two hair anchors; and
   severing the elongated metal tube at an intermediate location along the at least two slits such that a first portion of each of the at least two slits is contained in one of the at least two hair anchors and a second portion of each of the at least two slits remains attached to the elongated metal tube for inclusion in a subsequent hair anchor to be later severed from the elongated metal tube.

2. The process of claim 1, further including laser cutting the at least two slits into the elongated metal tube.

3. The process of claim 1, further including inserting a hair strand into the elongated metal tube prior to severing the elongated metal tube.

4. The process of claim 1, wherein the at least two slits cooperate to define at least two resilient members.

5. The process of claim 4, further including a tubular body portion undissected by the at least two slits, and wherein the at least two resilient members are integral with and extend from the tubular body portion.

6. The process of claim 5, further including forming a slot across the intermediate location along each slit, the slot being configured to facilitate severing of the metal tube at the intermediate location.

7. The process of claim 6, further including forming at least one burr upon severance at the intermediate location.

8. The process of claim 5, further including forming a notch between two adjacent tubular body portions in the elongated metal tube, and wherein the notch is configured to facilitate severing of the elongated metal tube at a location of the notch.

9. The process of claim 8, further including forming at least one burr at a location of severance of the notch.

10. The process of claim 5, wherein prior to severing at the intermediate location, the at least two resilient members extend between two tubular body portions of two prospective hair anchors.

11. The process of claim 4, further including deforming the at least two resilient members to cause the at least two resilient members to diverge from a longitudinal axis of the elongated metal tube prior to severing the elongated metal tube at the intermediate location.

12. The process of claim 1, wherein forming at least two slits includes cutting a first slit in a wall of the elongated metal tube, the first slit extending in a direction of a longitudinal axis of the elongated metal tube, and cutting a second slit in the tube, the second slit opposing the first slit.

\* \* \* \* \*